(12) United States Patent
Chen (10) Patent No.: US 11,819,605 B2
(45) Date of Patent: Nov. 21, 2023

(54) ELECTRONIC CIGARETTE WITH DUST-PROOF AND ANTI-LEAKING ARRANGEMENT

(71) Applicant: Yushui Chen, Quanzhou (CN)

(72) Inventor: Yushui Chen, Quanzhou (CN)

( * ) Notice: Subject to any disclaimer, the term of this patent is extended or adjusted under 35 U.S.C. 154(b) by 1188 days.

(21) Appl. No.: 16/448,646

(22) Filed: Jun. 21, 2019

(65) Prior Publication Data

US 2020/0390159 A1     Dec. 17, 2020

(30) Foreign Application Priority Data

Jun. 12, 2019 (CN) .......................... 201910508217.6
Jun. 12, 2019 (CN) .......................... 201920880718.2

(51) Int. Cl.
    *A24F 40/40*         (2020.01)
    *A24F 40/10*         (2020.01)
    *A61M 11/04*        (2006.01)
    *A61M 15/06*        (2006.01)

(52) U.S. Cl.
    CPC ........... *A61M 11/042* (2014.02); *A61M 15/06* (2013.01)

(58) Field of Classification Search
    CPC ..... A61M 15/06; A61M 11/042; A24F 40/00; A24F 40/10; A24F 40/40
    See application file for complete search history.

(56) References Cited

U.S. PATENT DOCUMENTS

| | | | |
|---|---|---|---|
| 2007/0045288 A1* | 3/2007 | Nelson ................. | A61M 11/041 219/533 |
| 2013/0167854 A1* | 7/2013 | Shin ........................ | A24F 40/42 131/329 |
| 2016/0050975 A1* | 2/2016 | Worm ..................... | A24F 15/01 131/328 |

FOREIGN PATENT DOCUMENTS

CN            203789159 U   *   8/2014

* cited by examiner

*Primary Examiner* — Alex B Efta
(74) *Attorney, Agent, or Firm* — Novoclaims Patent Services LLC; Mei Lin Wong (57) ABSTRACT

An electronic cigarette assembly, which includes a housing with a top cover, a cigarette body which includes a battery, an atomizer, a cartridge, and a mouthpiece supported by a cigarette housing, an opener unit which includes a pair of first track member at the housing, a pair of second rack member at the cigarette housing, pair of gear communicating between the pair of first rack member and the pair of second rack member respectively, an elongated bar member communicating with the top cover to control the top cover to an open position or a close position, an atomizer control unit which comprises a control bar member, a position guiding member, and a guiding groove for turning on and off the atomizer simultaneously when moving to the open position and the closed position respectively.

19 Claims, 8 Drawing Sheets

ELECTRONIC CIGARETTE WITH DUST-PROOF AND ANTI-LEAKING ARRANGEMENT

BACKGROUND OF THE PRESENT INVENTION

Field of Invention

The present invention relates to an electronic cigarette, and more particularly to an electronic cigarette assembly which has dust-proof and leakage prevention arrangement.

Description of Related Arts

In recent years, the market of electronic cigarettes grows rapidly. In general, an electronic cigarette includes a battery, an atomizer, a cartridge for e-liquid storage and a mouthpiece. When electronic cigarettes are carried from places to places inside a pocket or a handbag, leaking of e-liquid from the electronic cigarette becomes a serious problem to the users. There are different causes for the leakage such as temperature changes, coil or parts damages, or improper positioning of the electronic cigarettes. Therefore it is not possible to predict or prevent the leakage when it happens.

Dust is inevitable but a problem which may affect the function of the atomizer. Once the e-cigarette is exposed, dust will be present.

SUMMARY OF THE PRESENT INVENTION

An object of the present invention is to provide an electronic cigarette assembly which has a leak-proof and dust-proof arrangement so that leakage or dust will not be a problem to the user.

Additional advantages and features of the invention will become apparent from the description which follows, and may be realized by means of the instrumentalities and combinations particular point out in the appended claims.

According to the present invention, the foregoing and other objects and advantages are attained by an electronic cigarette assembly, comprising:

a housing having a receiving cavity and a top opening, and comprising a top cover sealing the top opening in a closed position and uncovering the top opening in an open position;

a cigarette body which comprises a battery, an atomizer, a cartridge, and a mouthpiece supported by a cigarette housing, the cigarette body receiving inside the receiving cavity of the housing in such a manner that the cigarette body is completely inside the receiving cavity at the closed position and is partially received inside the receiving cavity of the housing at the open position to expose the mouthpiece of the cigarette body;

an opener unit comprising at least one first track member mounted on the housing, at least one second rack member mounted on the cigarette housing corresponding to the first track member, at least one gear communicating between the first rack member and the second rack member so that a movement of the housing will lead to a movement of the cigarette body, an elongated bar member having a mounting end mounted on the gear and a free end opposite to the mounting end communicating with the top cover, wherein the elongated bar member is capable of moving together with the gear, and a movement of the housing will actuate a movement of the gear and the elongated bar member, and the free end of the elongated bar is capable of opening the top cover to the open position; and an atomizer control unit communicating with the atomizer, which comprises a control bar member moveably connected to the cigarette housing of the cigarette body, a position guiding member protruded from the control bar member, and a guiding groove provided on the housing for guiding and stopping a movement of the position guiding member so that a maximum distance of upward movement and a maximum distance of downward movement of the position guiding member is defined by the guiding groove.

Preferably, the housing is formed by an inner housing and an outer housing moveably connected to the inner housing, and the first track member is positioned at the outer housing.

Preferably, the inner housing comprises an outer panel and an inner panel coupled with the outer panel, and has a side opening, the outer housing comprises an outer member and a bottom inner member connected to the outer member at a bottom side thereof, and a pair of sliding connectors provided at two sides of the outer housing, the outer member of the outer housing covers the inner panel of the inner housing such that the outer housing is capable of sliding along a longitudinal direction relative to the inner housing through the pair of sliding connectors.

Preferably, the elongated bar member further comprises a spring so that the elongated bar member can spring along the longitudinal direction.

Preferably, the gear is a stepped gear wheel having two complete circular sets of teeth.

Preferably, the atomizer comprises a control switch, the control bar member presses against the control switch at the closed position to stop oil and gas passage and turn off the atomizer and releases the control switch at the open position to turn on the atomizer.

Preferably, the control switch is a protrude button extended outside the cigarette casing, the cigarette housing has a sliding groove receiving the control bar member such that the control bar member is capable of sliding movement along the sliding groove.

When the electronic cigarette assembly is at the closed position, a downward sliding movement of the outer housing by pressing the outer member of the outer housing downwardly causes the cigarette body to move upwardly through the opener unit and the top cover to open while the control bar member movers upwardly and stopped by the guiding groove and the cigarette body continues to move upwardly and the protruded button of the control switch is released and then the atomizer is turned on, and the mouthpiece of the cigarette body is exposed outside the housing.

When the electronic cigarette assembly is at the open position, an upward sliding movement of the outer housing by pressing the outer member of the outer housing upwardly causes the cigarette body to move downwardly through the opener unit while the control bar member movers downwardly and stopped by the guiding groove to press against the protruded button of the control switch and then the atomizer is turned off, and the mouthpiece of the cigarette body moves back inside the housing and the top cover is returned to the closed position.

Accordingly, the electronic cigarette assembly is well-protected by the housing at the closed position to prevent dust or leakage problem. The electronic cigarette can easily and conveniently slide from the closed position to the open position for use, or slide from the open position to the closed position to carry.

Still further objects and advantages will become apparent from a consideration of the ensuing description and draw-

DETAILED DESCRIPTION OF THE PREFERRED EMBODIMENT

Referring to FIG. 1 to FIG. 8 of the drawings, an electronic cigarette assembly 100 comprises a housing 20, a cigarette body 40 received inside the housing 20, an opener unit 50 communicating between the housing 20 and the cigarette body 40. The housing 20 can effectively provide a dust-proof and a leak-proof function to the electronic cigarette assembly 100 when the electronic cigarette assembly 100 is in a closed position at which the cigarette body 40 is completely received inside the housing 20.

Figure 4:
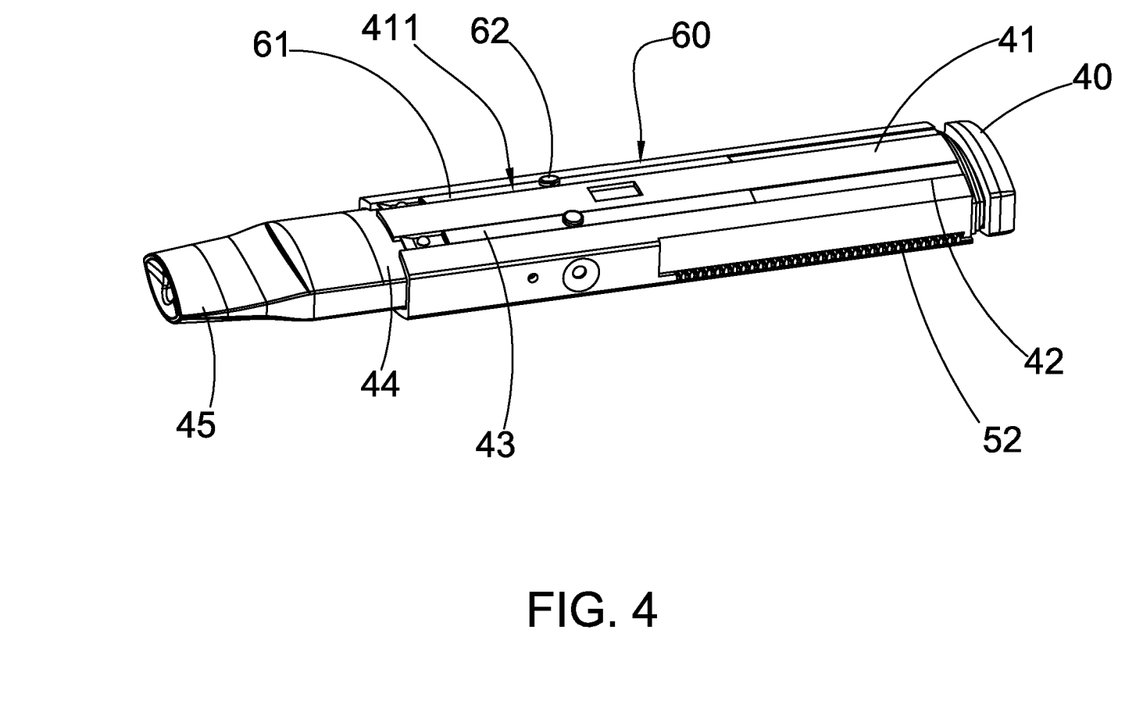
FIG. 4 is a perspective view of a cigarette body of the electronic cigarette according to the above preferred embodiment of the present invention.

The cigarette body 40 comprises a cigarette housing 41, a battery 42, an atomizer 43 connected to the battery 42, a cartridge 44 for e-liquid storage and a mouthpiece 45. The battery 42, the atomizer 43, the cartridge 44 and the mouthpiece 45 are supported by the cigarette housing 41.

Figure 7:
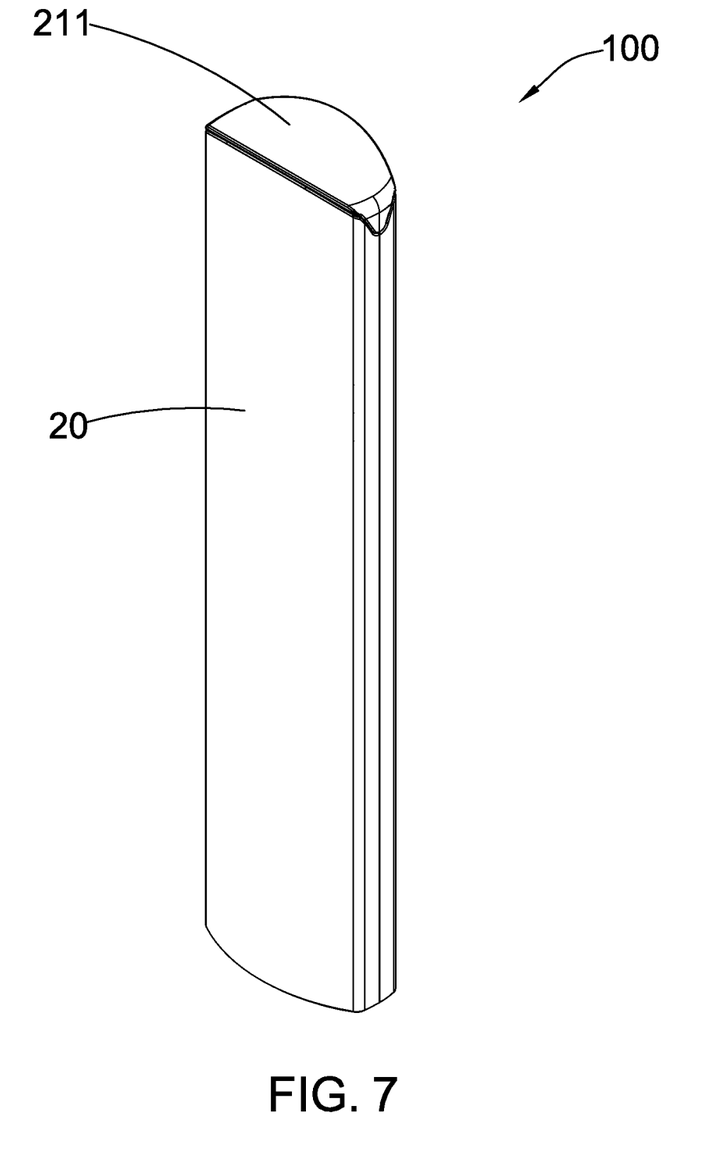
FIG. 7 is a perspective view of the electronic cigarette assembly shown in a closed position according to the above preferred embodiment of the present invention.
Figure 8:
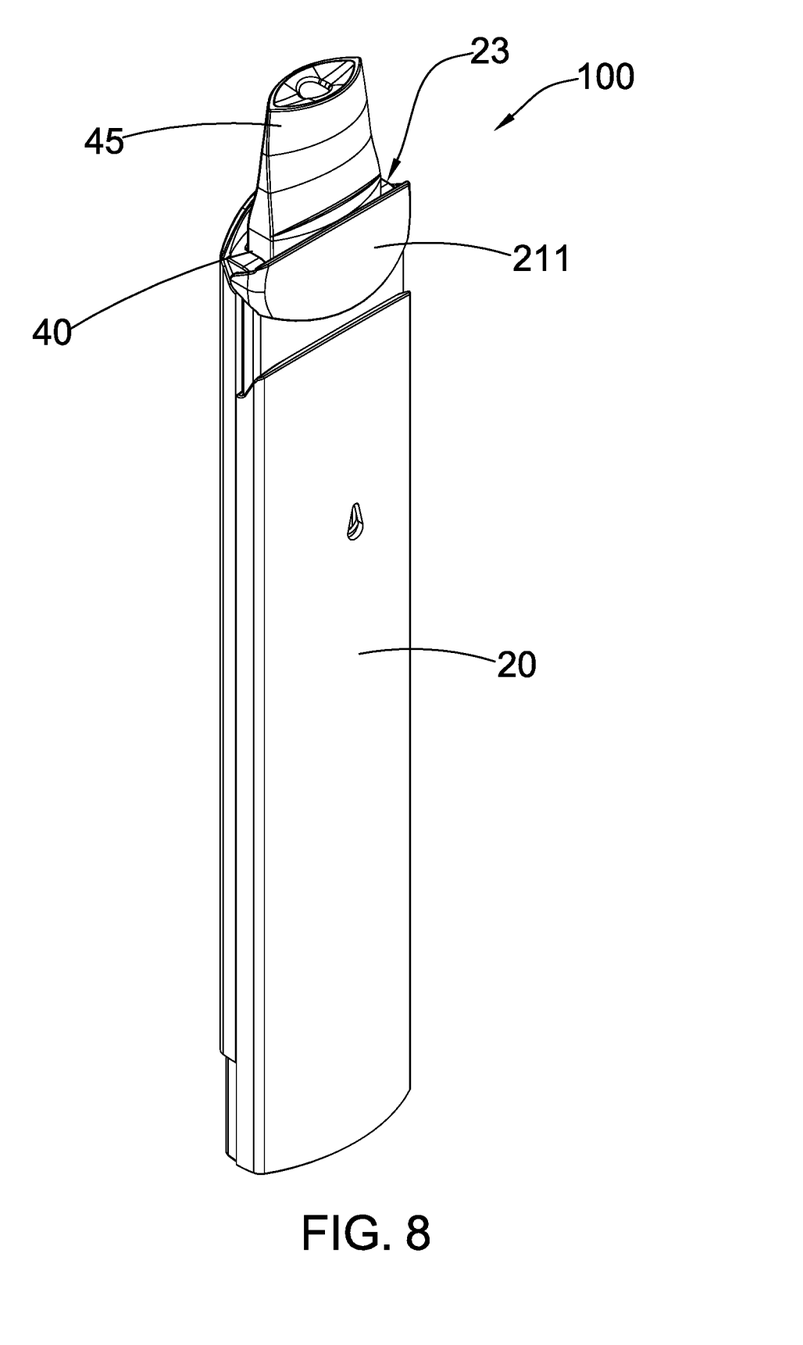
FIG. 8 is a perspective view of the electronic cigarette assembly shown in an open position according to the above preferred embodiment of the present invention.

The mouthpiece 45 is exposed outside the housing 20 of the electronic cigarette assembly 100 while the atomizer 43 is turned on when the electronic cigarette assembly 100 is in an open position, as shown in FIG. 8 of the drawings. The entire cigarette body 40 is received inside the housing 20 of the electronic cigarette assembly 100 while the atomizer 43 is turned off when the electronic cigarette assembly 100 is in the closed position, as shown in FIG. 7 of the drawings.

In particular, the atomizer 43 comprises a control switch 431 to control the on and off position of the atomizer 43. The atomizer 43 is turned on when the electronic cigarette assembly 100 is in the open position and is turned off when the electronic cigarette assembly 100 is in the close position.

The housing 20 comprises an inner housing 21 and an outer housing 22 connected to the inner housing 21 and defines a receiving cavity 23 for receiving the cigarette body 40.

Figure 3:
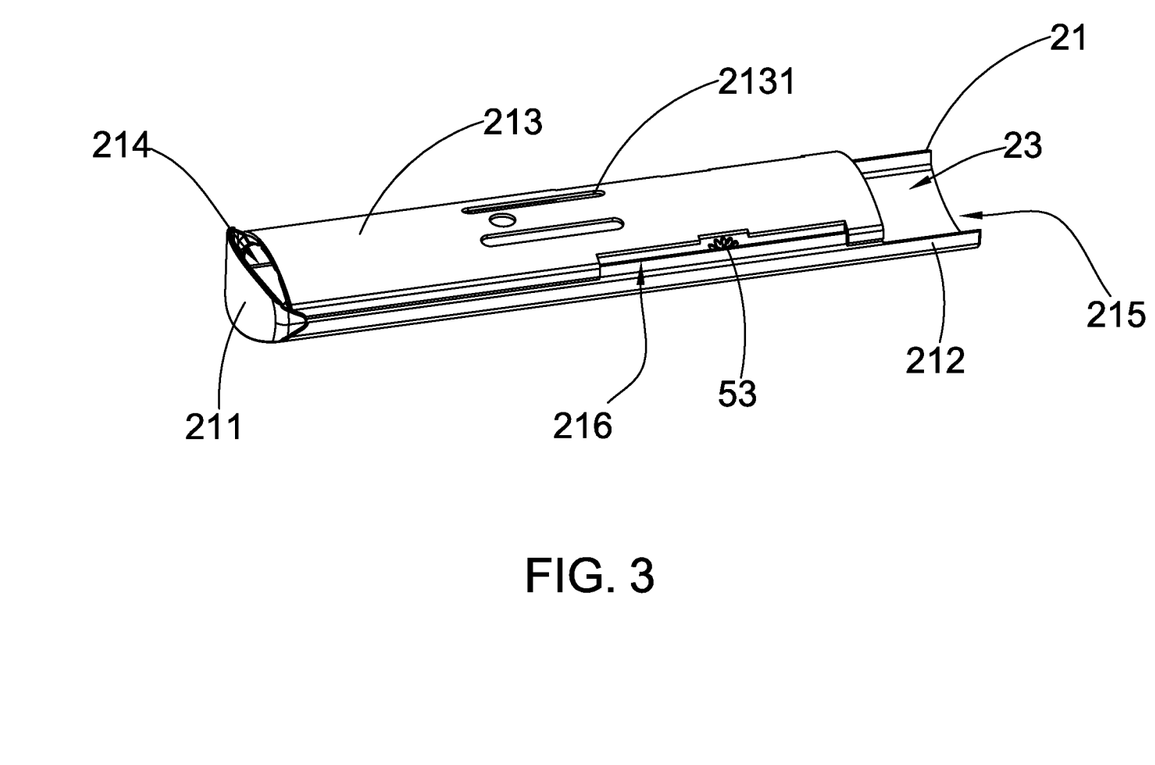
FIG. 3 is a perspective view of an inner housing of the electronic cigarette according to the above preferred embodiment of the present invention.

The inner housing 21 comprises an outer panel 212, an inner panel 213 coupled with the outer panel 212 to define a top opening 214, a bottom opening 215, and at least one side opening 216, a top cover 211 moveably connected through the inner panel 213 and the outer panel 212 arranged for covering the top opening 214 in the closed position and for exposing the top opening 214 in the open position.

Figure 1:
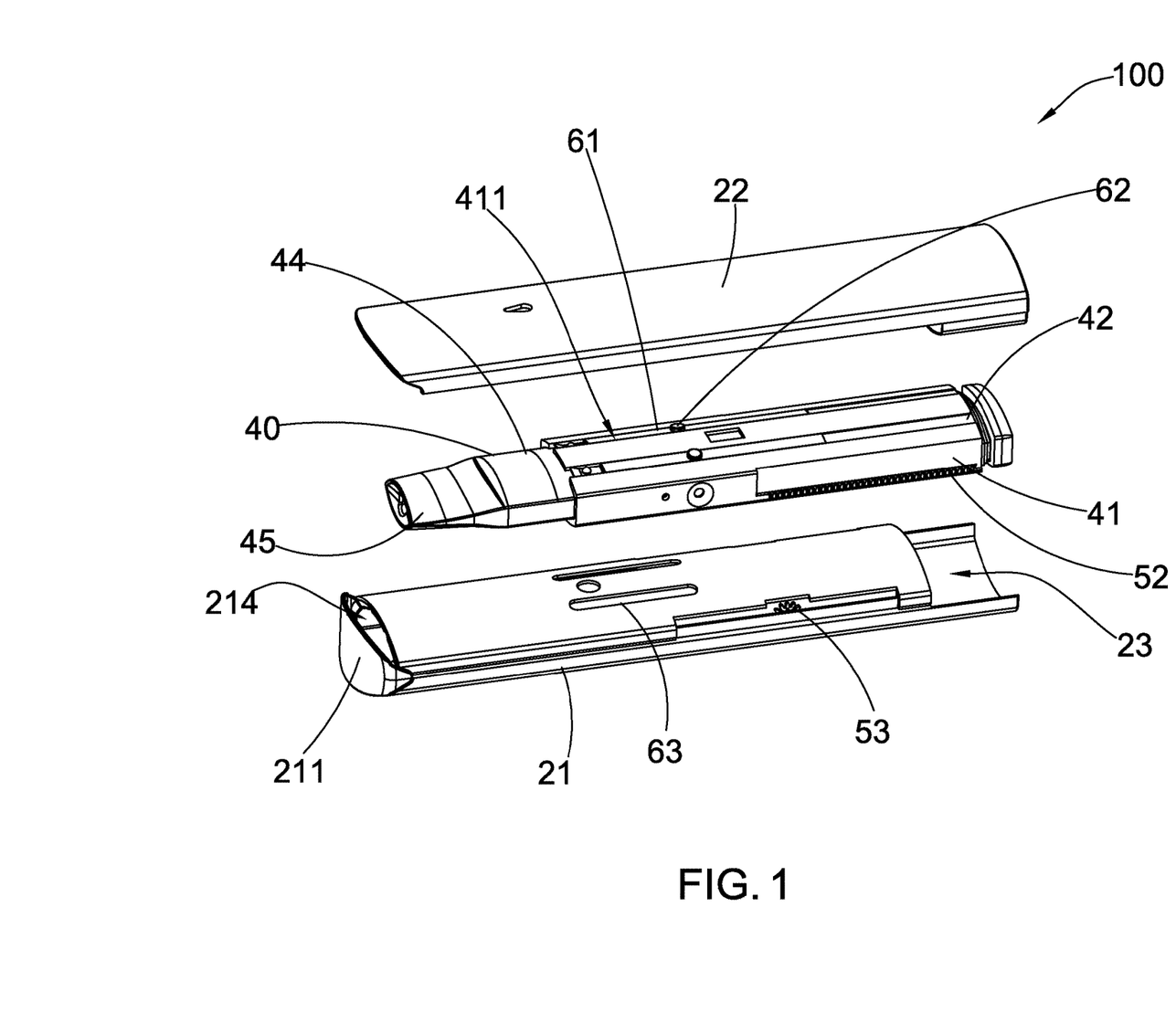
FIG. 1 is a schematic partially exploded view of an electronic cigarette assembly according to a preferred embodiment of the present invention.
Figure 2:
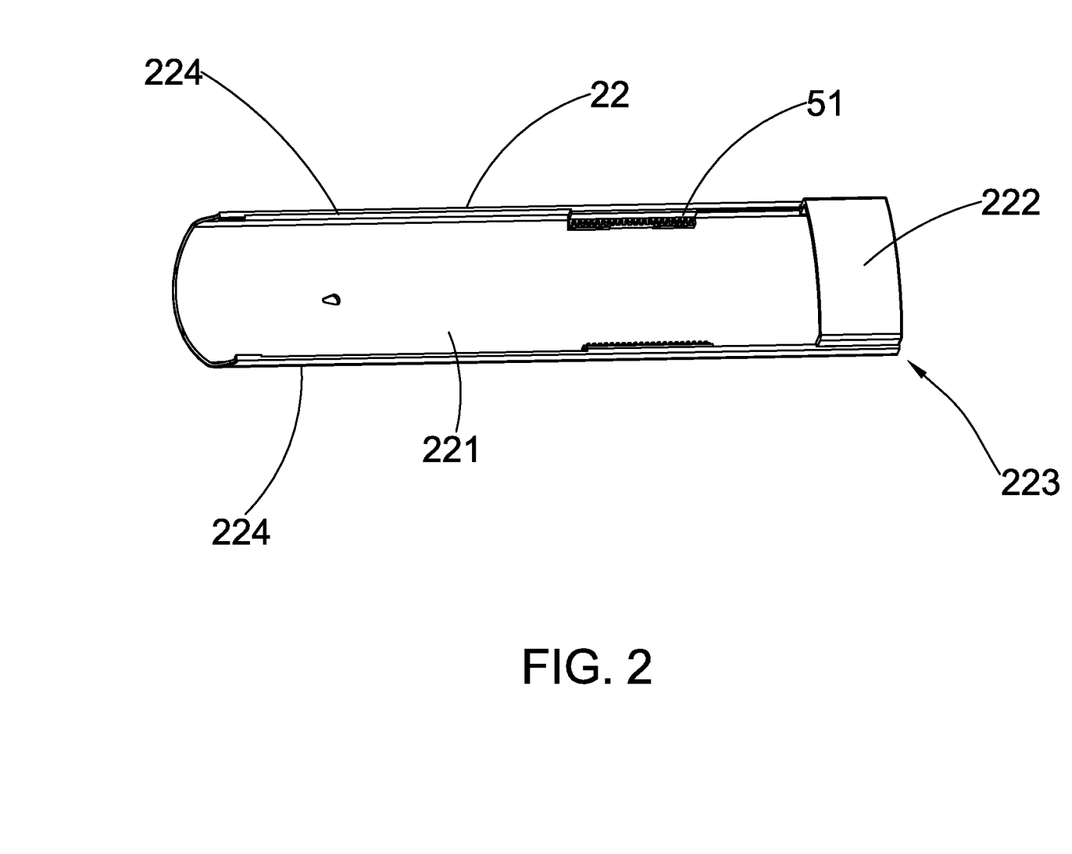
FIG. 2 is a perspective view of an outer housing of the electronic cigarette according to the above preferred embodiment of the present invention.

The outer housing 22 comprises an outer member 221, a bottom inner member 222 connected to the outer member 221 at a bottom side 223 of the outer housing 22, and a pair of sliding connectors 224 at two sides of the outer housing 22. In particular, the bottom inner member 222 covered the bottom opening 215 of the inner housing 21 and the outer member 221 of the outer housing 22 covers the inner panel 213 of the inner housing 21 such that the sliding connectors 224 of the outer housing 22 is capable of connecting to and having sliding movement relative to the inner housing 21 along a longitudinal direction, namely an up and down movement.

Figure 5:
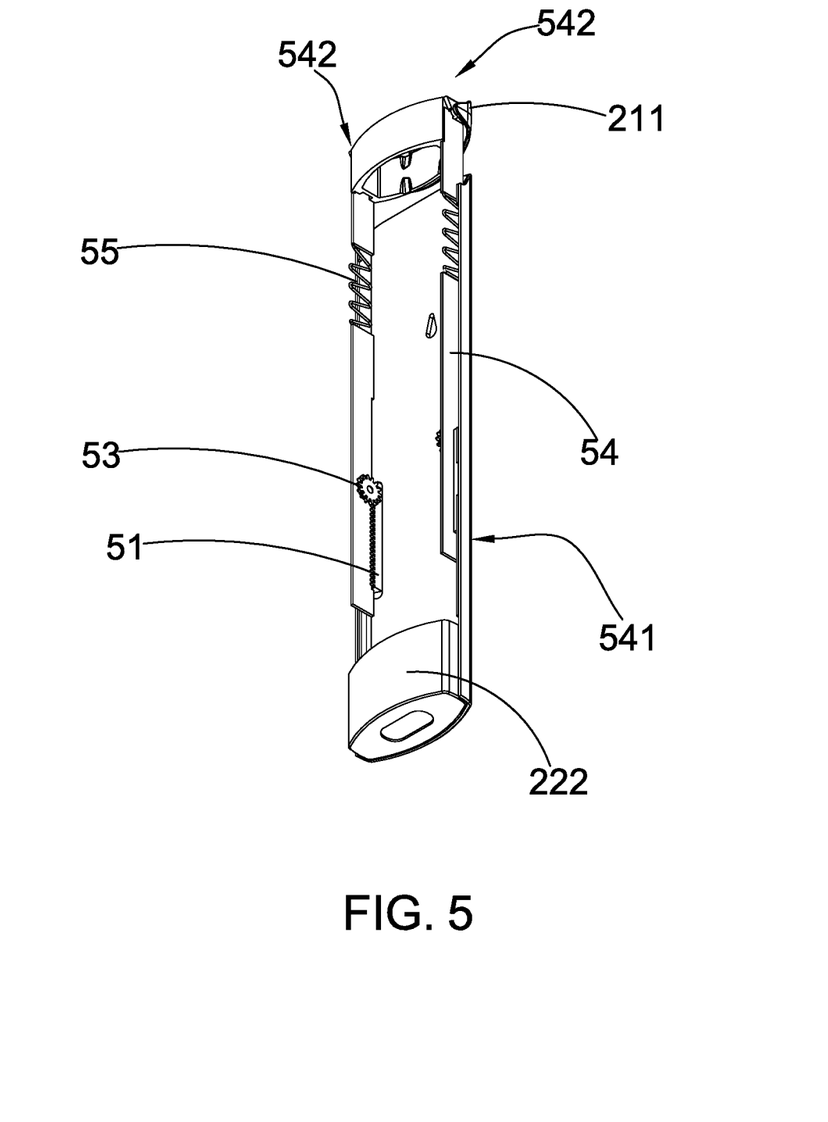
FIG. 5 is a perspective view showing an opener unit of the electronic cigarette according to the above preferred embodiment of the present invention.

The opener unit 50 comprises a first rack member 51 mounted along one side of the outer member 221 of the outer housing 22, a second rack member 52 mounted along one side of the cigarette housing 41, a gear 53 communicating between the first rack member 51 and the second rack member 52, an elongated bar member 54 having one end mounted to the gear 53 arranged to move together with the gear 53 and comprising a spring member 55. In particular, the gear 53 is a stepped gear wheel and the upward and downward movement of the bar member 54 is controlled by the gear 53. The side opening 217 of the inner housing 21 has an elongated structure and is arranged for receiving the first rack member 51 when the inner housing 21 and the outer housing 22 are coupled together.

It is worth mentioning that at least one set of one first rack member 51, one second rack member 52, one gear 53, one elongated bar member 54, and one spring member 55 is included in the present invention. Preferably, a pair first rack member 51, a pair of corresponding second rack member 52, a pair of corresponding gear 53, a pair of corresponding elongated bar member 54, and a pair of corresponding spring member 55 are included in the present invention, which are shown in FIGS. 1-8 of the drawings.

Preferably, the elongated bar member 54 has a mounting end 541 mounted on the gear 53 and a free end 542 opposite to the mounting end 541 communicating with the top cover 211. The elongated bar member 54 is capable of moving together with the gear 53, and a movement of the housing will actuate a movement of the gear and the elongated bar member, and the free end of the elongated bar member 54 pushes the top cover 211 to the open position, which is shown in FIG. 5 of the drawings.

When a user presses the outer housing 22 to slide downwardly, the first rack member 51 guide the gear 53 to move upward such that movement is transmitted to the cigarette body 40 through the cigarette housing 41 and the cigarette body 40 is moved upwardly at a uniform speed, then the elongated bar member 54 is moved upwardly such that the elongated bar member 54 biases against the top cover 211 and pushes the top cover 211 to the open position.

Figure 6:
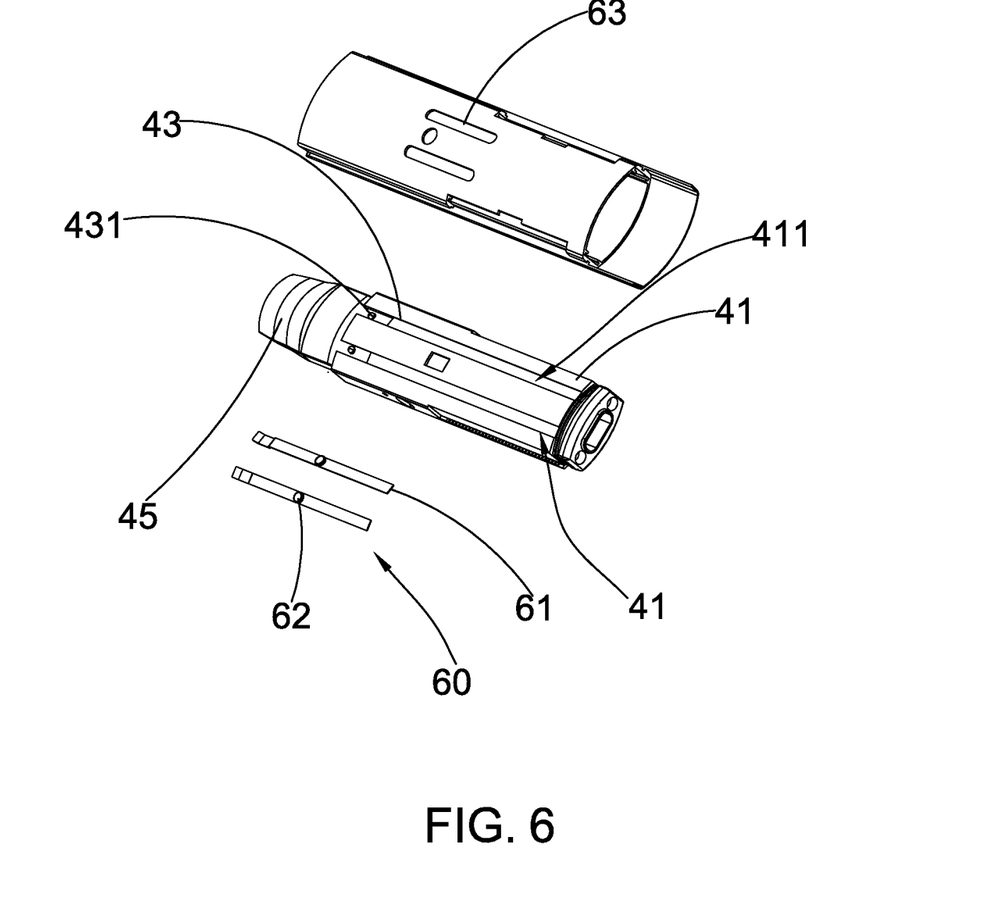
FIG. 6 is a schematic view showing an atomizer control unit of the electronic cigarette according to the above preferred embodiment of the present invention.

The atomizer control unit 60 comprises a control bar member 61 slidably connected to the cigarette housing 41, a position guiding member 62 on the control bar member 61, and a guiding groove 63 provided on said inner housing 21 for guiding a position of the guiding member 62. In particular, the control bar member 61 has an elongated structure capable of having a sliding movement and the position guiding member 62 is a protruded element slidably connected to the guiding groove 63 so that the upward and downward movement of the position guiding member 62 is restricted by the guiding groove 63. When the cigarette assembly 100 is in the closed position, the control bar member 61 is arranged to press against the control switch 431 of the atomizer 43 so that the atomizer 43 is turned off. When the cigarette assembly is in the open position, the control bar member 61 is moved away from the control switch 431 of the atomizer 43 so that the control switch 431 is free from pressing force of the control bar member 61 and so the atomizer 43 is turned on.

In other words, when a user presses the outer housing 22 to slide downwardly to open the cigarette assembly 100, the mouthpiece 45 is moved upwardly and exposed outside the housing 20 while the atomizer 43 is turned on simultaneously through the atomizer control unit 60. In particular, when the cigarette body 40 is guided to move upwardly through the opener unit 50, the control bar member 61 moves together with the cigarette body 40 until the upward movement of the position guiding member 62 is limit by the guiding groove 63, then the cigarette body 40 continues to move upwardly while the control bar member 61 is stopped by the guiding groove 63 and can no longer press against the atomizer switch 431. Then, the atomizer switch 631 can spring open and the atomizer 43 is turned on.

When a user presses the outer housing 22 to slide upwardly to close the cigarette assembly 100, the cigarette body 40 is moved downwardly to position inside the housing completely and the control bar member 61 presses against the atomizer switch 431 so that the atomizer 43 is turned off. In particular, when a user presses the outer housing 22 to slide upwardly to close the cigarette assembly 100, the mouthpiece 45 is moved downwardly to receive inside the housing 20 while the atomizer 43 is turned off simultaneously through the atomizer control unit 60. In particular, when the cigarette body 40 is guided to move downwardly through the opener unit 50, the control bar member 61 moves together with the cigarette body 40 until the downward movement of the position guiding member 62 is limit by the guiding groove 63, then the cigarette body 40 continues to move downwardly while the control bar member 61 is stopped by the guiding groove 63 and press against the atomizer switch 431 so that the oil and gas passage path is stopped by the atomizer switch 431 and the atomizer 43 is turned off Preferably, as shown in FIG. 6 of the drawings, the cigarette housing 41 comprises a sliding groove 411 receiving the control bar member 61 and the position guiding member 62 is protruded from the control bar member 61 and is received in the guiding groove 63.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An electronic cigarette assembly, comprising: a housing having a receiving cavity and a top opening, and comprising a top cover sealing said top opening in a closed position and uncovering said top opening in an open position; a cigarette body which comprises a battery, an atomizer, a cartridge, and a mouthpiece supported by a cigarette housing, said cigarette body received_inside said receiving cavity of said housing in such a manner that said cigarette body is completely inside said receiving cavity at the closed position and is partially received inside said receiving cavity of said housing at the open position to expose the mouthpiece of said cigarette body;

an opener unit comprising at least one first track member mounted on said housing, at least one second track member mounted on said cigarette housing corresponding to said at least one first track member, at least one gear communicating between said at least one first track member and said at least one second track member so that a movement of said housing will lead to a movement of said cigarette body, an elongated bar member having a mounting end mounted on said at least one gear and a free end opposite to said mounting end communicating with said top cover, wherein said elongated bar member is capable of moving together with said at least one_gear, and a movement of said housing will actuate a movement of said at least one gear and said elongated bar member, and said free end of said elongated bar is capable of opening said top cover to the open position;

and an atomizer control unit communicating with said atomizer, which comprises a control bar member moveably connected to said cigarette housing of said cigarette body, a position guiding member protruded from said control bar member, and a guiding groove provided on said housing for guiding and stopping a movement of said position guiding member so that a maximum distance of upward movement and a maximum distance of downward movement of said position guiding member is defined by said guiding groove.

2. The electronic cigarette assembly according to claim 1, wherein said housing is formed by an inner housing and an outer housing moveably connected to said inner housing, and said at least one first track member is positioned at said outer housing.

3. The electronic cigarette assembly according to claim 2, wherein said inner housing comprises an outer panel and an inner panel coupled with said outer panel, and has a side opening, said outer housing comprises an outer member and a bottom inner member connected to said outer member at a bottom side thereof, and a pair of sliding connectors provided at two sides of said outer housing, said outer member of the said outer housing covers said inner panel of the inner housing such that said outer housing is capable of sliding along a longitudinal direction relative to said inner housing through said pair of sliding connectors.

4. The electronic cigarette assembly according to claim 3, wherein said elongated bar member further comprises a spring so that said elongated bar member can spring along the longitudinal direction.

5. The electronic cigarette assembly according to claim 1, wherein said at least one gear is a stepped gear wheel having two complete circular sets of teeth.

6. The electronic cigarette assembly according to claim 4, wherein said at least one gear is a stepped gear wheel having two complete circular sets of teeth.

7. The electronic cigarette assembly according to claim 1, wherein said atomizer comprises a control switch, said control bar member presses against said control switch at the closed position to stop oil and gas passage and turn off said atomizer and releases said control switch at the open position to turn on said atomizer.

8. The electronic cigarette assembly according to claim 3, wherein said atomizer comprises a control switch, said control bar member presses against said control switch at the closed position to stop oil and gas passage and turn off said atomizer and releases said control switch at the open position to turn on said atomizer.

9. The electronic cigarette assembly according to claim 5, wherein said atomizer comprises a control switch, said control bar member presses against said control switch at the closed position to stop oil and gas passage and turn off said atomizer and releases said control switch at the open position to turn on said atomizer.

10. The electronic cigarette assembly according to claim 6, wherein said atomizer comprises a control switch, said control bar member presses against said control switch at the closed position to stop oil and gas passage and turn off said atomizer and releases said control switch at the open position to turn on said atomizer.

11. The electronic cigarette assembly according to claim 7, wherein said control switch is a protrude button extended outside said cigarette said cigarette housing has a sliding groove receiving said control bar member such that said control bar member is capable of sliding movement along said sliding groove.

12. The electronic cigarette assembly according to claim 9, wherein said control switch is a protrude button extended outside said cigarette housing, said cigarette housing has a sliding groove receiving said control bar member such that said control bar member is capable of sliding movement along said sliding groove.

13. The electronic cigarette assembly according to claim 10, wherein said control switch is a protrude button extended outside said cigarette housing, said cigarette housing has a sliding groove receiving said control bar member such that said control bar member is capable of sliding movement along said sliding groove.

14. The electronic cigarette assembly according to claim 10, wherein when said electronic cigarette assembly is at said closed position, a downward sliding movement of said outer housing by pressing said outer member of said outer housing downwardly causes said cigarette body to move upwardly through said opener unit and said top cover to open while said control bar member moves upwardly and stopped by said guiding groove and said cigarette body continues to move upwardly and said control switch is released and then said atomizer is turned on, and said mouthpiece of said cigarette body is exposed outside said housing.

15. The electronic cigarette assembly according to claim 13, wherein when said electronic cigarette assembly is at said closed position, a downward sliding movement of said outer housing by pressing said outer member of said outer housing downwardly causes said cigarette body to move upwardly through said opener unit and said top cover to open while said control bar member movers upwardly and stopped by said guiding groove and said cigarette body continues to move upwardly and control switch is released and then said atomizer is turned on, and said mouthpiece of said cigarette body is exposed outside said housing.

16. The electronic cigarette assembly according to claim 10, wherein when said electronic cigarette assembly is at said open position, an upward sliding movement of said outer housing by pressing said outer member of said outer housing upwardly causes said cigarette body to move downwardly through said opener unit while said control bar member movers downwardly and stopped by said guiding groove to press against said control switch and then said atomizer is turned off, and said mouthpiece of said cigarette body moves back inside said housing and said top cover is returned to the closed position.

17. The electronic cigarette assembly according to claim 13, wherein when said electronic cigarette assembly is at said open position, an upward sliding movement of said outer housing by pressing said outer member of said outer housing upwardly causes said cigarette body to move downwardly through said opener unit while said control bar member movers downwardly and stopped by said guiding groove to press against said control switch and then said atomizer is turned off, and said mouthpiece of said cigarette body moves back inside said housing and said top cover is returned to the closed position.

18. The electronic cigarette assembly according to claim 14, wherein when said electronic cigarette assembly is at said open position, an upward sliding movement of said outer housing by pressing said outer member of said outer housing upwardly causes said cigarette body to move downwardly through said opener unit while said control bar member movers downwardly and stopped by said guiding groove to press against said control switch and then said atomizer is turned off, and said mouthpiece of said cigarette body moves back inside said housing and said top cover is returned to the closed position.

19. The electronic cigarette assembly according to claim 15, wherein when said electronic cigarette assembly is at said open position, an upward sliding movement of said outer housing by pressing said outer member of said outer housing upwardly causes said cigarette body to move downwardly through said opener unit while said control bar member movers downwardly and stopped by said guiding groove to press against said control switch and then said atomizer is turned off, and said mouthpiece of said cigarette body moves back inside said housing and said top cover is returned to the closed position.

* * * * *